(12) United States Patent
Nelson

(10) Patent No.: US 6,261,540 B1
(45) Date of Patent: *Jul. 17, 2001

(54) CYCLODEXTRINS AND HYDROGEN PEROXIDE IN DENTAL PRODUCTS

(75) Inventor: Dennis G. A. Nelson, Mountain Lakes, NJ (US)

(73) Assignee: Warner-Lambert Company, Morris Plains, NJ (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/175,864

(22) Filed: Oct. 20, 1998

Related U.S. Application Data

(60) Provisional application No. 60/062,991, filed on Oct. 22, 1997.

(51) Int. Cl.$^7$ ............................... A61K 7/16; A61K 7/20
(52) U.S. Cl. ............................... 424/53; 424/49
(58) Field of Search ............................... 424/49–88

(56) References Cited

U.S. PATENT DOCUMENTS

| | | | |
|---|---|---|---|
| 4,267,166 | * 5/1981 | Yajima | 426/650 |
| 4,332,825 | * 6/1982 | Miyawaki et al. | 426/330.5 |
| 4,420,471 | * 12/1983 | Elton et al. | 424/49 |
| 4,431,631 | 2/1984 | Clipper et al. | 424/53 |
| 4,684,517 | 8/1987 | Clipper et al. | 424/52 |
| 4,727,064 | 2/1988 | Pitha | 514/58 |
| 4,971,797 | * 11/1990 | Cherukuri et al. | 424/440 |
| 5,095,035 | 3/1992 | Eby, III | 514/494 |
| 5,186,926 | 2/1993 | Williams et al. | 424/53 |
| 5,236,699 | 8/1993 | Libin | 424/54 |
| 5,296,216 | 3/1994 | Turner | 424/53 |
| 5,300,251 | * 4/1994 | Osa et al. | 252/182.13 |
| 5,302,373 | * 4/1994 | Giacin, I et al. | 424/49 |
| 5,310,545 | 5/1994 | Douglas | 424/53 |
| 5,330,749 | * 7/1994 | Giacin, II et al. | 424/49 |
| 5,382,571 | * 1/1995 | Granger | 514/58 |
| 5,626,837 | * 5/1997 | Shimada et al. | 424/49 |
| 5,635,238 | * 6/1997 | Trinh et al. | 426/650 |
| 5,753,770 | * 5/1998 | Breitenbaum | 525/326.1 |
| 5,905,067 | * 5/1999 | Chapman et al. | 510/368 |
| 5,945,087 | * 8/1999 | Nelson et al. | 424/49 |
| 5,945,088 | * 8/1999 | Delli Santi et al. | 424/49 |

FOREIGN PATENT DOCUMENTS

| | | |
|---|---|---|
| 803 243 | * 10/1997 | (EP) . |
| 5341440 | 4/1978 | (JP) . |
| 54145268 | * 11/1979 | (JP) . |
| 01190623 | * 7/1989 | (JP) . |
| 07238008 | * 9/1995 | (JP) . |
| 9416674 | 8/1994 | (WO) . |
| 9418939 | 9/1994 | (WO) . |
| 95/34276 | * 12/1995 | (WO) . |
| 96/16633 | * 6/1996 | (WO) . |
| 96/29047 | * 9/1996 | (WO) . |
| 97/13495 | * 4/1997 | (WO) . |
| 97/26855 | * 7/1997 | (WO) . |
| 9726855 | 7/1997 | (WO) . |
| 97/30685 | * 8/1997 | (WO) . |

OTHER PUBLICATIONS

Abstracts of Kernoczi Herba Hung 23 (1–2) 109–125 Alteration of the Composition of Essential Oils by Cyclodextrin Complex for Mation Thymus Vulgaris Oil, 1984.*

Kooama et al Nippon Shokuhin Kogyo Gakkaishi 38(1): 49–54 White Cloud Precipitates Found in Syrup of Orange Cirtus Juice/Segments With/Without Addition of Cyclodextrin, 1991.*

* cited by examiner

*Primary Examiner*—Shep K. Rose
(74) *Attorney, Agent, or Firm*—Darryl C. Little; Evan J. Federman; Grover F. Fuller, Jr.

(57) ABSTRACT

Oral rinse and dentifrice compositions, comprising a mint flavor, mint flavor ingredient, citrus flavor, citrus flavor ingredient, phenolic ingredient, or mixtures thereof, said phenolic ingredient selected from the group consisting of menthol, eucalyptol, methyl salicylate, thymol, triclosan, and mixtures thereof; a cyclodextrin selected from the group consisting of hydroxypropyl β-cyclodextrin, hydroxyethyl β-cyclodextrin, hydroxypropyl γ-cyclodextrin, hydroxyethyl γ-cyclodextrin, α-cyclodextrin, methyl β-cyclodextrin, and mixtures thereof; and from about 0.1% by weight to about 10% by weight of hydrogen peroxide. These compositions are useful in retarding the development of plaque, treating gingivitis, and in treating the presence of micro-organisms in the oral cavity.

18 Claims, No Drawings

CYCLODEXTRINS AND HYDROGEN PEROXIDE IN DENTAL PRODUCTS

This non-provisional application is based upon claims priority from U.S. Provisional Application No. 60/062,991 filed Oct. 22, 1997.

BACKGROUND OF THE INVENTION

The present invention relates to dental products comprising cyclodextrins and hydrogen peroxide.

Dental plaque is present to some degree, in the form of a film, on virtually all dental surfaces. It is a by-product of microbial growth, and comprises a dense microbial layer consisting of a mass of micro-organisms embedded in a polysaccharide matrix. The micro-organisms present in plaque are mainly coccoidal organisms, particularly in early plaque. As plaque ages and matures, gram negative anaerobes and filamentous organisms appear and become more common after a few days. Plaque itself adheres to dental surfaces and may not be removed completely even with a rigorous brushing regimen and can build up, for example, in recessed areas of tooth surfaces, such as approximal regions and fissures. Moreover, plaque rapidly reforms on the tooth surface after it is removed.

Plaque may form on any part of the tooth surfaces, and can be found particularly at the gingival margin, in pits and fissures in the enamel, and on the surface of dental calculus. The danger associated with the formation of plaque on the teeth lies in the tendency of plaque to build up and eventually contribute to gingivitis, periodontitis and other types of periodontal disease, as well as dental caries and dental calculus.

More specifically, dental plaque is a precursor to the formation of the hard crystalline build up on teeth referred to as dental calculus. Both the bacterial and the non-bacterial components of plaque mineralize to form calculus, which comprises mineralized bacteria as well as organic constituents, such as epithelial cells, live bacteria, salivary proteins, leukocytes, and crystalline substances containing both calcium and phosphorous, e.g., hydroxyapatite, $Ca_{10}(PO_4)_6(OH)_2$, octacalcium phosphate, $Ca_8(HPO_4)_2(PO_4)_4.5H_2O$, brushite, $CaHPO_4.2H_2O$, and whitlockite, which is considered to have the formula $\beta\text{-}Ca_3(PO_4)_2$. Dental plaque and, hence, calculus are particularly prone to form at the gingival margin, i.e., the junction of the tooth and gingiva. The buildup of plaque at, and below, the gingival margin is believed to be the prime cause of gingivitis and periodontal disorders.

Mouthwashes have been formulated to contain antimicrobial ingredients whose function is to reduce the buildup of plaque, either by the direct bactericidal action (i.e. killing) on plaque and salivary micro-organisms and by bacteriostatic action (i.e. growth inhibition) on plaque and salivary micro-organisms. Scheie, A. AA. (1989) Modes of Action of Currently Known Chemical Anti-Plaque Agents Other than Chlorhexidine. J. Dent. Res. 68 Special Issue: 1609–1616.

However phenolics useful in oral compositions have low aqueous solubilities which limit their use in oral compositions and they require high levels of either 1) alcohol; 2) surfactants; or 3) co-solvents or combinations of the above for sufficient solubility in the carrier. PCT Appln No. WO 94/16674.

For example, thymol has been used as a anthelmintic and antiseptic, in mouthwashes containing a combination of menthol, methyl salicylate, eucalyptol and thymol. Oral compositions including mouthwashes and dentifrices containing phenolic compounds are referred to in U.S. Pat. No. 4,945,087; WO 94/16.16,674; WO 94/07477; and WO 94/18939. Triclosan (2,4,4'-trichloro-2'-hydroxydiphenyl ether) is a phenolic, nonionic antimicrobial agent used in various soap and toiletry products. In the oral care area, triclosan has been used as a plaque-inhibitory agent in various toothpastes and mouthrinses. Oral composition including triclosan are referred to in the following: U.S. Pat. Nos. 4,892,220; 5,032,386; 5,037,637; 5,034,154; 5,080,887; 5,236,699; 5,043,154; 5,032,385; and 5,156,835 as well as EPO 85303216.7.

Cyclodextrins are known to form inclusion complexes with various compounds. The cyclodextrin molecule consists of glucopyranose units arranged in a torus-like or donut-like configuration having all the secondary hydroxyl groups located on one side of the torus and all primary hydroxyl groups located on the other side. Alpha, beta, and gamma cyclodextrin contain 6, 7 & 8 cyclic glucopyranose units, respectively, in the torus shell. The "lining" of the internal cavity is formed by hydrogen and glucosidic oxygen-bridge atoms and therefore the surface is slightly apolar.

Hydrogen peroxide has been used in oral compositions, for example, in U.S. Pat. Nos. 4,431,631; 4,537,778; 4,684,517; 5,104,644; 5,174,990; 5,186,926; 5,296,216 and 5,310,546, and PCT International Application WO 97/26855. Hydrogen peroxide and other peroxygens including carbamide peroxide, sodium percarbonate and sodium perborate have been used for treating certain oral disorders such as, oral malodor, dental plaque, gingivitis, aphthous ulcers and for controlling post-surgical infections and the like.

Hydrogen peroxide and other peroxygens tend to be unstable with storage, although this can be reduced at acidic pHs, and that interaction of peroxygens with other excipients in oral formulations can cause their degradation. In particular, certain flavors, including peppermint, spearmint and citrus flavors are known to be unstable in the presence of peroxygens (See, U.S. Pat. No. 4,537,778). Also flavor ingredients such as menthofurane and flavor terpenes are unstable or can react with peroxygens. In U.S. Pat. No. 5,186,926 it is stated that menthol has some slight susceptibility to oxidation and preferably should not be formulated with a peroxygen compound. Also, methyl salicylate can hydrolyze in aqueous solutions. To overcome these incompatibility and degradation problems, numerous solutions have been proposed: 1) Using dual-phase packaging to isolate coreactive ingredients into separate compartments (U.S. Pat. Nos. 4,528,180; 4,849,213; 5,186,926); 2) Physical encapsulation of the peroxygen or the peroxide-sensitive excipient to protect against degradation by co-reactive ingredients.

We have found that these degradation problems can be greatly reduced, without the need for dual-phase packaging or physical encapsulation, by using soluble cyclodextrins described in detail below. When incorporated into the composition at the correct amount, the soluble cyclodextrins form inclusion complexes with the flavor or phenolic compounds protecting them from rapid degradation from the peroxygen co-ingredients. Thus, this invention stabilizes formulations which use peroxygens together with flavor/phenolic compounds within the same hydroalcoholic/aqueous composition. We have found that combinations of peroxygens with phenolic antimicrobials formulated in oral compositions are especially effective, with respect to bactericidical activity, against a broad spectrum of oral micro-organisms. However, until this invention, there was no easy way to formulate these ingredients into a single-phase, stable, aqueous composition.

SUMMARY OF THE INVENTION

The present invention relates to an oral composition in the form of a stable oral rinse or dentifrice (e.g., a toothpaste or gel), comprising:

a) from about 0.01% to about 10% by weight of a mint flavor, mint flavor ingredient, citrus flavor, citrus flavor ingredient, phenolic ingredient, or mixtures thereof, said phenolic ingredient selected from the group consisting of menthol, eucalyptol, methyl salicylate, thymol, triclosan, and mixtures thereof;

b) from about 0.1% by weight to about 60% by weight of a soluble cyclodextrin, said soluble cyclodextrin selected from the group consisting of hydroxypropyl β-cyclodextrin, hydroxyethyl β-cyclodextrin, hydroxypropyl γ-cyclodextrin, hydroxyethyl γ-cyclodextrin, α-cyclodextrin, methyl β-cylodextrin, and mixtures thereof, c) up to about 25% by weight ethanol;

d) from about 0.1% by weight to about 10% by weight of hydrogen peroxide; and e) an orally acceptable carrier.

The present also relates to a method for retarding development of plaque on a dental surface in the oral cavity of a mammal, comprising administering to said dental surface an amount of said oral composition effective in retarding said development of plaque.

The present also relates to a method of treating gingivitis, comprising administering to a mammal in need of such treatment an amount of said oral composition effective in treating gingivitis.

The present also relates to a method of treating the presence of micro-organisms in the oral cavity of a mammal, comprising administering to the mammal in need of such treatment an amount of said oral composition effective in reducing the viable population of said micro-organisms.

The present also relates to a method for treating oral malodor, comprising administering to the mammal in need of such treatment an amount of an oral composition effective in treating oral malodor.

The present also relates to a method for treating apthous ulcers, comprising administering to the mammal in need of such treatment an amount of an oral composition effective treating apthous ulcers.

The present also relates to a method for treating post-surgical oral infections, comprising administering to the mammal in need of such treatment an amount of an oral composition effective in treating post-surgical oral infections.

DETAINED DESCRIPTION OF THE INVENTION

Compositions of the present invention include low-alcohol oral care compositions (oral rinse compositions and dentifrices, e.g. a toothpaste or gel) that contain cyclodextrin compounds which solubilize phenolic antimicrobial compounds. As a result of higher levels of solubilized phenolics in a solution, the phenolic compounds have improved bio-availability in treating plaque, as well as providing compositions having excellent low-temperature stability. These compositions retard the development of plaque as well as treat gingivitis and periodontal diseases without the use of high alcohol levels, high surfactant levels or the use of other co-solvents.

Phenolics useful as antimicrobials in the present invention and effective in treating micro-organisms present in the oral cavity of a mammal include menthol, menthol derivatives (e.g. methone, isomenthone, menthyl acetate, neomenthol and isomenthol), methyl salicylate, eucalyptol, thymol and triclosan. Thymol and triclosan are generally considered to have the best antimicrobial activity of these phenolics.

Citrus flavors that may be employed in this invention include natural and synthetic citrus oils, for example, orange, grapefruit, lemon, mandarin orange, lime, Mexican lime, tangerine, tangelo and blends thereof, as well as citrus aromatics, natural oleo resins, and extracts. Examples of citrus flavors with natural and synthetic ingredients include Carrubba A9047 (an orange flavor) and Noville AN110099 (a citrus mint flavor). These flavors typically contain one or more citrus flavor ingredients including, for example, the following: d-limonene, l-limonene, dl-limonene, alpha-citral and beta-citral (geranol), α-terpinene, γ-terpinene, 2-dodecanal, α-pinene, β-pinene, 2-pentenal, cadiene, decylaldehyde, linalool, terpineol, linalyl esters, terpinyl acetate, citronellal, decanal, as well as $C_8$ to $C_{10}$ and $C_{12}$ aldehydes, acids, and esters found in citrus flavors, and mixtures thereof. Either the natural or synthetic form of these ingredients could be used in the composition of the present invention. Citrus flavor and citrus flavor ingredients may have some effect on masking the unpleasant taste of phenolics.

Certain of these ingredients may provide a better masking effect of the phenolics in these compositions either alone or in combination with other citrus oil components. For example, terpenes found in citrus flavors may be particularly effective in masking the unpleasant phenolic taste found in these compositions. Limonene is the most abundant terpene in citrus flavor and can be found at levels of approximately 90–95% in citrus flavors. It is possible that this terpene could be an important contributor to masking the unpleasant taste of phenolics by citrus oils. One hypothetical mechanism for the masking ability of citrus oils is that the chemical structure of d-limonene and its isomers is similar to several of the phenolics (e.g. thymol, menthol and eucalytol). Thus, limonene may act as an antagonist to phenolic compounds for taste receptors on the tongue.

Mint flavors that may be employed in this invention include natural and synthetic flavors selected from the group consisting of peppermint, spearmint, and wintergreen. These flavors typically contain one or more mint flavor ingredients including, for example, the following: menthol, menthol derivatives (e.g. methone, isomenthone, menthyl acetate, neomenthol and isomenthol), carron, carron derivatives (e.g. dihydrocarrone, carveol, carveol, carveol acetate and terpenes), limonene, methofuran, eucalytol, α-pinene, β-pinene, terpinenes, piperitone, and pulegone.

The claimed compositions utilize from about 0.01% to about 10% by weight of these mint flavors, mint flavor ingredients, citrus flavors, citrus flavor ingredients, phenolic ingredients, or mixtures thereof. For oral rinses, these mint flavors, mint flavor ingredients, citrus flavors, citrus flavor ingredients, phenolic ingredients, or mixtures thereof preferably range from about 0.01% by weight to about 0.5% by weight. For dentifrices, the amount of these mint flavors, mint flavor ingredients, citrus flavors, citrus flavor ingredients, phenolic ingredient, or a mixture thereof preferably range from about 0.5% by weight to about 2% by weight. Some of the components named in the above catagories may be included in under more than one catagory. For example, menthol and menthol derivatives are included as both a phenolic ingredient and as a mint flavor ingredient, and limonene is included as both a mint flavor ingredient and a citrus flavor ingredient.

Molecules, or functional groups of molecules having molecular dimensions that match the cyclodextrin cavity, being less hydrophilic (i.e. more hydrophobic) than water, will position themselves in the cyclodextrin cavity at the expense of water molecules. In aqueous solutions, the slightly apolar cyclodextrin cavity is occupied by water molecules which are energetically unfavored (polar-apolar interaction) and are therefore readily substituted by appropriate "guest molecules" which are less polar than water. In the case of the present invention, the "guest molecules" are the phenolic ingredients mentioned above.

Suitable cyclodextrins useful in the present invention include hydroxypropyl β-cyclodextrin, hydroxyethyl β-cyclodextrin, hydroxypropyl γ-cyclodextrin, hydroxyethyl γ-cyclodextrin, α-cycodextrin and methyl β-cyclodextrin. Suitable candidate cyclodextrins typically have to have an aqueous solubility of at least about 10% by weight and form sufficiently soluble phenolic-cyclodextrin complexes to be suitable for this invention. Hydroxypropyl β-cyclodextrin is the preferred cyclodextrin.

Each of the seven cyclic glucopyranose units in β-cyclodextrin contains three hydroxyl groups in the 2-, 3- and 6-positions, which can be etherified. In the case of the partially etherified cyclodextrin derivatives used in this invention, only some of these positions are substituted with hydroxyethyl or hydroxypropyl groups. A wide range of substitutions can be made per molecule up to a maximum of 18. The preferred range of substitution ranges from about 0.5 to 8 positions. Thus, hydroxypropyl β-cyclodextrin is a chemically modified cyclodextrin consisting of an amorphous isomeric mixture of thousands of geometric and optical isomers with varying degrees of substitution and varying numbers of hydroxypropyl substituents, however the size of the cyclodextrin cavity is constant for these isomers.

The amount of cyclodextrin ranges from about 0.1% by weight to about 60% by weight and is selected from the group consisting of hydroxypropyl β-cyclodextrin, hydroxyethyl β-cyclodextrin, hydroxypropyl γ-cyclodextrin, hydroxyethyl γ-cyclodextrin, α-cyclodextrin, methyl β-cyclodextrin, and mixtures thereof are useful for the invention. For oral rinses, the amount of soluble cyclodextrin preferably ranges from about 0.1% by weight to about 25% by weight, more preferably from about 1% by weight to about 5% by weight. For dentifrices, the amount of soluble cyclodextrin preferably ranges from about 1% by weight to about 50% by weight, more preferably from about 5% by weight to about 30% by weight.

The amount of hydrogen peroxide ranges from about 0.1% by weight to about 10% by weight. The amount of hydrogen peroxide for oral rinses should preferably range from about 0.25% by weight to about 3% by weight. The amount of hydrogen peroxide in the dentifrices should preferably range from about 1% by weight to about 10% by weight.

For dentifrice compositions suitable abrasives include precipitated silica or silica gels which have an average particle size ranging from about 0.1 to about 50 microns. Preferred silica abrasives include those marketed under the tradename "Sylodent®" or "Syloid®" by the W. R. Grace & Co. and those marketed under the tradename "Zeodent®" by the J. M. Huber Corp. Other suitable abrasives, having a suitable particle size as described above, include β-phase calcium pyrophosphate, alumina and calcium carbonate. The amount of abrasive in a dentifrice composition ranges up to about 60% by weight, preferably from 10% by weight to 40% by weight.

Dentifrice and oral rinse compositions also may contain a suitable fluoride source. Typical sources include soluble salts of the fluoride ion; e.g. sodium fluoride, potassium fluoride, stannous fluoride, stannous fluorozirconate etc.; or, soluble salts of the monofluorophosphate ion; e.g. sodium monofluorophosphate etc. The preferred fluoride source is sodium fluoride. The fluoride ion source should be sufficient to provide from about 50 ppm to about 2,500 ppm fluoride, preferably from about 250 ppm to about 1500 ppm for dentifrices and from about 50 ppm to about 250 ppm fluoride for oral rinses.

A liquid carrier for oral rinses generally includes mixtures of water and ethanol, although the carrier can be alcohol-free, especially in dentifrices. For oral rinses, the amount of water ranges upwards from about 25% by weight. The amount of alcohol ranges by weight from about 0% to about 25% by weight, preferably from about 0% by weight to about 15% by weight. For dentifrices, the amount of water ranges from about 0% by weight to about 60% by weight, preferably from about 0% by weight to about 40% by weight.

The pH of the oral compositions can range from about 4.0 to about 8.0.

The oral rinse compositions, for example, Examples 1 and 2, are unusually stable so as to be substantially clear and substantially free of precipitation, flocculation, or crystal formation at about room temperature (about 25° C.) as well as at low temperatures of at least about 5° C. for at least about 1 week. The low temperature stability of these compositions is determined by cooling the compositions to about 5° C., storing for at least seven days and determining whether any precipitate, crystallized or flocculated material is formed in the clear compositions (solutions and gels).

Oral surfactants useful in the present invention include nonionic and anionic surfactants. Oral surfactants employed include block co-polymers of polyoxyethylene and polyoxypropylene such as the Pluronics from BASF. Other oral surfactants include soluble alkyl sulfonates having 10 to 18 carbon atoms, such as sodium lauryl sulfate, and sulfates of monoglycerides of fatty acids having 10 to 18 carbon atoms or sarcosinates (including salts and derivatives) such as sodium-N-lauroyl sarcosinate. Mixtures of anionic and nonionic surfactants can be used. These ingredients are generally present from about 0% by weight to about 4% by weight, preferably from about 0% by weight to about 1% by weight for oral rinses and from about 0.5% by weight to about 4% by weight for dentifrices.

Additional anticalculus agents can be optionally added to the compositions. These include tetra-alkali or di-alkali metal pyrophosphate salts and zinc salts, such as, but not limited to, zinc chloride etc. These optional anticalculus agents are generally present at levels ranging from about 0% by weight to about 10% by weight for pyrophosphate salts and from about 0% by weight to about 3% by weight for zinc salts.

In compositions relating to the invention, preservatives may be used, especially for non-alcohol or low alcohol compositions. These include benzoic acid, sodium benzoate, methylparaben, propylparaben, sorbic acid and potassium sorbate. These optional preservative agents are generally present at levels ranging from about 0% by weight to about 2% by weight.

In compositions relating to the invention, buffering systems may be used to stabilize the pH in the product. Typical buffering systems include, but are not limited to, citrate, benzoate, gluconate and phosphate. Buffering systems are present in concentrations from about 0.01% by weight to about 1% by weight In addition to the above ingredients, the invention may include other optional ingredients to impart desired mouth feel and provide flavoring and coloring.

Humectants are an optional component of the compositions. For oral rinses they impart a moist and elegant feel to the mouth and in toothpaste compositions they prevent hardening on exposure to air. Some humectants can provide sweetness to the composition. Suitable humectants include edible polyhydric alcohols such as glycerin, sorbitol, propylene glycol and xylitol. The humectant generally is present in an amount ranging from 0% by weight to 30% by weight for oral rinses and 0% by weight to 70% by weight for dentifrice compositions.

Thickening agents or binders are an optional component of the compositions. Typical thickening include, xanthan gum, carrageenan, carboxyvinyl polymers, carbomers, cellulose gums such as carboxymethyl cellulose, cellulose derivatives such as hydroxyethylcellulose and silicas. Thickeners are usually present in the compositions from about 0% by weight to 2% by weight. Xanthan gum is the preferred thickener in oral rinses. In dentifrices, silica-based thickeners can be used at concentrations from 0% by weight to about 20% by weight. "Sylox®" by W. R. Grace & Co. is the tradename of the preferred silica-based thickener.

Flavoring agents can be added to the compositions. The flavorant may be a flavoring oil or mixture of flavoring oils such as oil of peppermint, spearmint, wintergreen, clove, sassafras, lemon, orange or lime. Sweetening agents such as saccharin, lactose, maltose, aspartame, sodium cyclamate, polydextrose etc. can be added to the compositions. Flavoring agents generally are present in an amount ranging from 0.001% by weight to about 0.5% by weight for oral rinses and from 0.25% by weight to about 5% by weight for dentifrice compositions. Sweetening agents generally are present in an amount ranging from 0.001% by weight to about 5% by weight for oral rinse and dentifrice compositions. Coloring agents generally are present in an amount ranging from 0% by weight to 0.01 % by weight.

EXAMPLE 1

The following dental rinse was formulated: Poloxamer 407, sodium citrate, citric acid, sodium saccharin, sorbitol solution 70%, hydroxypropyl β-cyclodextrin, and dye were dissolved in water at room temperature (approximately 25° C.), using a mixer with a high lift blade rotating at approximately 200–300 rpm to give a clear aqueous solution. Benzoic acid, menthol, thymol, methyl salicylate, eucalyptol, and flavor were added to the 190° alcohol to give a clear alcoholic solution. The alcoholic phase was added slowly to the aqueous phase which was continually agitated until the addition was complete. Hydrogen peroxide solution was added to the aqueous/alcoholic phases which was continually agitated until addition was complete. The resulting blue-green product was mixed for a further 20 minutes. The product had a pH of approximately 4.0.

| Ingredient | Weight Percent |
| --- | --- |
| poloxamer 407 | 0.50 |
| sodium citrate | 0.04 |
| citric acid | 0.01 |
| sorbitol (70%) | 20.00 |

-continued

| Ingredient | Weight Percent |
| --- | --- |
| FD + C green no. 3 | 0.0006 |
| hydroxylpropyl β-cyclodextrin | 1.25 |
| sodium saccharin | 0.03 |
| alcohol, 190 proof | 8.00 |
| benzoic acid | 0.15 |
| thymol | 0.064 |
| eucalyptol | 0.092 |
| menthol | 0.042 |
| methyl salicylate | 0.060 |
| flavor | 0.10 |
| hydrogen peroxide | 0.75 |
| water | q.s. |
| total | 100.0000 |

EXAMPLE 2

The following dental rinse was formulated: Poloxamer 407, sodium citrate, citric acid, sodium lauryl sulfate, sodium saccharin, sorbitol solution 70%, hydroxypropyl β-cyclodextrin, and dye were dissolved in water at room temperature, using a mixer with a high lift blade rotating at approximately 200–300 rpm to give a clear aqueous solution. Benzoic acid, menthol, thymol, methyl salicylate, eucalyptol, and flavor were added to the 190° alcohol to give a clear alcoholic solution. The alcoholic phase was added slowly to the aqueous phase which was continually agitated until the addition was complete. Hydrogen peroxide was added to the aqueous/alcoholic phases which was continually agitated until addition was complete. The resulting blue-green product was mixed for a further 20 minutes. The product had a pH of approximately 4.0.

| Ingredient | Weight Percent |
| --- | --- |
| poloxamer 407 | 0.50 |
| sodium lauryl sulfate | 0.25 |
| sodium citrate | 0.04 |
| citric acid | 0.01 |
| sorbitol (70%) | 20.00 |
| FD + C green no. 3 | 0.0006 |
| sodium saccharin | 0.03 |
| alcohol, 190 proof | 8.00 |
| benzoic acid | 0.15 |
| thymol | 0.064 |
| eucalyptol | 0.092 |
| menthol | 0.042 |
| methyl salicylate | 0.060 |
| flavor | 0.10 |
| hydrogen peroxide | 0.75 |
| water | q.s. |
| total | 100.0000 |

What is claimed is:

1. An aqueous oral composition in the form of an oral rinse or dentifrice in the form of a gel packaged in a single compartment container without the need for physical encapsulation of: a) hydrogen peroxide or b) a peroxide sensitive component to protect against degradation by co-reactive ingredients, comprising:
   a) from about 0.01% to about 10% by weight of a mint flavor, mint flavor ingredient, citrus flavor, citrus flavor ingredient, or phenolic ingredient, said phenolic ingredient is selected from the group consisting of menthol, menthol derivatives, mint flavor ingredient, eucalyptol, methyl salicylate, thymol, triclosan, and mixtures thereof;

b) from about 0.1% by weight to about 60% by weight of a soluble cyclodextrin, said soluble cyclodextrin selected from the group consisting of hydroxypropyl β-cyclodextrin, hydroxyethyl β-cyclodextrin, hydroxypropyl γ-cyclodextrin, hydroxyethyl β-cyclodextrin, α-cyclodextrin, methyl β-cyclodextrin, and mixtures thereof;

c) from 0 to about 25% by weight ethanol;

d) from about 0.1% by weight to about 10% by weight of hydrogen peroxide; and e) an orally acceptable carrier, wherein said composition is substantially stable at about room temperature.

2. An oral composition according to claim 1, wherein said citrus flavor is selected from the group consisting of orange, grapefruit, lemon, mandarin orange, lime, tangerine, and tangelo; and said citrus flavor ingredient is selected from the group consisting of limonene, citral, cadiene, decylaldehyde, linalool, terpineol, linalyl esters, terpinyl acetate, citronellal, α-terpinene, γ-terpinene, 2-dodecanal, α-pinene, β-pinene, 2-pentenal, decanal, and $C_8$ to $C_{10}$ and $C_{12}$ aldehydes, acids, and esters found in citrus flavors.

3. An oral composition according to claim 1, wherein said mint flavor is selected from the group consisting of peppermint, spearmint, and wintergreen; and said mint flavor ingredient is selected from the group consisting of menthol, menthol derivatives, carron, carron derivatives, limonene, methofuran, eucalytol, α-pinene, β-pinene, terpinenes, piperitone, and pulegone.

4. An oral composition according to claim 1, further including up to about 4% by weight of an orally acceptable surfactant selected from the group consisting of an anionic surfactant, a nonionic surfactant, or mixtures thereof.

5. An orally composition according to claim 4, wherein the amount of orally acceptable surfactant is up to about 1% by weight.

6. An oral composition according to claim 1, further including an orally acceptable anticalculus agent.

7. An oral composition according to claim 6, wherein the orally acceptable anticalculus agent includes up to about 10% by weight of a pyrophosphate pharmaceutically acceptable salt.

8. An oral composition according to claim 1, further including an orally acceptable suitable fluoride ion source sufficient to provide from about 50 ppm to about 2500 ppm fluoride.

9. An oral composition according to claim 1, wherein the carron derivatives are selected from a group consisting of dihydrocarrone, carveol, carveol, carveol acetate and terpenes.

10. An oral composition according to claim 3, wherein the menthol derivatives are selected from a group consisting of methone, isomenthone, menthyl acetate, neomenthol and isomenthol.

11. An aqueous oral rinse composition packaged in a single compartment container without the need for physical encapsulation of: a) hydrogen peroxide or b) a peroxide-sensitive component to protect against degradation by co-reactive ingredients, comprising:

a) from about 0.01% to about 0.5% by weight of a spearmint or citrus flavor or flavor/phenolic said phenolic selected from the group consisting eucalyptol, methyl salicylate, thymol, triclosan, and mixtures thereof, said citrus flavor is selected from the group consisting of orange, grapefruit, lemon, mandarin orange, lime, tangerine, and tangelo, said citrus flavor ingredient is selected from the group consisting of limonene, citral, cadiene, decylaldehyde, linalool, terpineol, linalyl esters, terpinyl acetate, citronellal, α-terpinene, γ-terpinene, 2-dodecanal, α-pinene, β-pinene, 2-pentenal, decanal, and $C_8$ to $C_{10}$ and $C_{12}$ aldehydes, acids, and esters found in citrus flavors, said mint flavor is selected from the group consisting of peppermint, spearmint, and wintergreen; and said mint flavor ingredient is selected from the group consisting of menthol, menthol derivatives, carron, carron derivatives, limonene, methofuran, eucalytol, α-pinene, β-pinene, terpinenes, piperitone, and pulegone;

b) from about 0.1% by weight to about 5% by weight of a soluble cyclodextrin, said soluble cyclodextrin selected from the group consisting of hydroxypropyl β-cyclodextrin, hydroxyethyl β-cyclodextrin, hydroxypropyl γ-cyclodextrin, hydroxyethyl β-cyclodextrin, α-cyclodextrin, methyl β-cyclodextrin, and mixtures thereof;

c) from 0 to about 25% by weight ethanol;

d) from about 0.25% by weight to about 3% by weight of hydrogen peroxide; and e) from 0 to about to by weight of an orally acceptable surfactant selected from the group consisting of an anionic surfactant, a nonionic surfactant, or mixtures thereof; and f) an orally acceptable carrier, wherein said composition is substantially stable at about room temperature.

12. An aqueous dentifrice in the form of a gel packaged in a single compartment container without the need for physical encapsulation of: a) hydrogen peroxide or b) a peroxide-sensitive component to protect against degradation by co-reactive ingredients, comprising:

a) from about 0.5% to about 2% by weight of a mint flavor, mint flavor ingredient, citrus flavor, citrus flavor ingredient, phenolic ingredient, or mixtures thereof, said phenolic ingredient selected from the group consisting of menthol, eucalyptol, methyl salicylate, thymol, triclosan, and mixtures thereof, said citrus flavor is selected from the group consisting of orange, grapefruit, lemon, mandarin orange, lime, tangerine, and tangelo, said citrus flavor ingredient is selected from the group consisting of limonene, citral, cadiene, decylaldehyde, linalool, terpineol, linalyl esters, terpinyl acetate, citronellal, α-terpinene, γ-terpinene, 2-dodecanal, α-pinene, β-pinene, 2-pentenal, decanal, and $C_8$ to $C_{10}$ and $C_{12}$ aldehydes, acids, and esters found in citrus flavors, said mint flavor is selected from the group consisting of peppermint, spearmint and wintergreen; and said mint flavor ingredient is selected from the group consisting of menthol, menthol derivatives, carron, carron derivatives, limonene, methofuran, eucalytol, α-pinene, β-pinene, terpinenes, piperitone, and pulegone;

b) from about 0.5% by weight to about 30% by weight of a soluble cyclodextrin, said soluble cyclodextrin selected from the group consisting of hydroxypropyl β-cyclodextrin, hydroxyethyl β-cyclodextrin, hydroxypropyl γ-cyclodextrin, hydroxyethyl β-cyclodextrin, α-cyclodextrin, methyl β-cyclodextrin, and mixtures thereof;

c) from about 1% by weight to about 10%l by weight of hydrogen peroxide;

d) from 0 to about 60% by weight of an orally acceptable dental abrasive;

e) from about 0.5% by weight to about 4% by weight of an orally acceptable surfactant selected from the group consisting of an anionic surfactant, a nonionic surfactant, or mixtures thereof;

f) an orally acceptable suitable fluoride ion source sufficient to provide from about 250 ppm to about 1500 ppm fluoride; and g) an orally acceptable carrier, wherein said composition is substantially stable at about room temperature.

13. A method for retarding development of plaque on a dental surface in the oral cavity of a mammal, comprising administering to said dental surface an amount of an oral composition according to claim 1 effective in retarding said development of plaque.

14. A method of treating gingivitis, comprising administering to a mammal in need of such treatment an amount of an oral composition according to claim 1 effective in treating gingivitis.

15. A method of treating the presence of micro-organisms in the oral cavity of a mammal, comprising administering to the mammal in need of such treatment an amount of an oral composition according to claim 1 effective in reducing the viable population of said micro-organisms.

16. A method for treating oral malodor, comprising administering to the mammal in need of such treatment an amount of an oral composition according to claim 1 effective in treating oral malodor.

17. A method for treating apthous ulcers, comprising administering to the mammal in need of such treatment an amount of an oral composition according to claim 1 effective treating apthous ulcers.

18. A method for treating post-surgical oral infections, comprising administering to the mammal in need of such treatment an amount of an oral composition according to claim 1 effective in treating post-surgical oral infections.

* * * * *